United States Patent
Roth

Patent Number: 6,096,175
Date of Patent: Aug. 1, 2000

[54] THIN FILM STENT

[75] Inventor: Noah M. Roth, San Clemente, Calif.

[73] Assignee: Micro Therapeutics, Inc., Irvine, Calif.

[21] Appl. No.: 09/118,729

[22] Filed: Jul. 17, 1998

[51] Int. Cl.[7] .................................................. C23C 14/34
[52] U.S. Cl. .............................. 204/192.15; 204/192.14; 204/192.23; 216/37; 216/87; 216/83; 148/559
[58] Field of Search .......................... 204/192.14, 192.15, 204/192.23; 216/37, 87, 89, 83; 623/1; 419/38, 49; 148/559

[56] References Cited

U.S. PATENT DOCUMENTS

| | | | |
|---|---|---|---|
| 3,945,903 | 3/1976 | Svendor et al. | |
| 4,180,448 | 12/1979 | Soshiki et al. | 204/192 |
| 4,582,559 | 4/1986 | Tanielian et al. | 156/603 |
| 4,591,482 | 5/1986 | Nyce | 419/38 |
| 4,740,207 | 4/1988 | Kreamer | 623/1 |
| 4,992,153 | 2/1991 | Bergmann et al. | 204/192 |
| 5,061,914 | 10/1991 | Busch et al. | 337/140 |
| 5,114,504 | 5/1992 | AbuJudom, II et al. | 148/402 |
| 5,306,294 | 4/1994 | Winston | 623/1 |
| 5,358,615 | 10/1994 | Grant et al. | 204/192.15 |
| 5,405,379 | 4/1995 | Lane | 623/1 |
| 5,441,515 | 8/1995 | Khosravi | 606/194 |
| 5,443,500 | 8/1995 | Sigwart | 623/1 |
| 5,597,458 | 1/1997 | Sanchez, Jr. et al. | 204/192.3 |
| 5,632,771 | 5/1997 | Boatman et al. | 623/1 |
| 5,635,144 | 6/1997 | Aklufi | 422/186.05 |
| 5,744,377 | 4/1998 | Sekiguchi et al. | 438/674 |
| 5,849,206 | 12/1998 | Amon et al. | 216/63 |
| 5,873,904 | 2/1999 | Ragheb et al. | 623/1 |

OTHER PUBLICATIONS

Kern et al, Deposition Technologies and Applications: Introduction and Overview, Thin–Film Deposition Processes and Techniques, Edited by Klaus K. Schuegraf, Noyer Publications, p. 1, 1996.

Chapman, et al, Introduction to Sputtering, Thin–Film Depostion Processes and Techniques, Edited by Klaus K. Schuegraf, Noyer Publications, p. 291, 1997.

Krulevitch et al., Thin Film Shape Memory Alloy Microactuators, 5 Journal of Microelectromechnical Systems, 270 (Dec. 1996).

Rogers et al., Microcontact Printing and Electroplating on Curved Substrates: Pruduction of Free–Standing Three–Dimensional Metallic Microstructures, 6 Advanced Mater. 475 (1997).

*Primary Examiner*—Maria Nuzzolillo
*Assistant Examiner*—Julian A Mercado
*Attorney, Agent, or Firm*—K. David Crockett, Esq; Crockett & Crockett

[57] ABSTRACT

A method for fabricating a stent or other medical device by creating a free standing thin film of metal.

14 Claims, 6 Drawing Sheets

Step A
Apply photoresist

Step B
Etch/Image and Develop
Waste layer

Step C
sputter film

Step D
Lift off: remove waste layer
and overlying film

THIN FILM STENT

FIELD OF THE INVENTION

The present invention relates to treatments for vascular diseases and other diseases of body lumens, in particular to a method of manufacturing a stent.

BACKGROUND OF THE INVENTION

The inventions described below were developed with the goal of providing new and better therapies for certain types of vascular disease for which the present day therapies are widely regarded as inadequate. Vascular disease includes aneurysms which can rupture and cause hemorrhage, atherosclerosis which can cause the occlusion of the blood vessels, vascular malformation and tumors. Occlusion of the coronary arteries, for example, is a common cause of heart attack. Vessel occlusion or rupture of an aneurysm within the brain are causes of stroke. Tumors fed by intra-cranial arteries can grow within the brain to the point where they cause a mass effect. The mass and size of the tumor can cause a stroke or the symptoms of stroke, requiring surgery for removal of the tumor or other remedial intervention.

The newly preferred therapy for coronary occlusions is placement of an expanded metal wire-frame, called a stent, within the occluded region of the blood vessel to hold it open. Stents of various construction have been proposed, including the Palmaz-Schatz™ balloon expandable metal stent, the Wallstent self-expanding braided metal stent, the Strecker knitted metal stent, the Instent™ coil stent, the Cragg coiled stent and the Gianturco Z stent. Stents have been proposed for treatment of atherosclerosis in the neck, but carotid endarterectomy is still the preferred treatment for stenosis. Most perioperative strokes are thought to be caused by technical errors during endarterectomy (see Becker, Should Metallic Vascular Stents Be Used To Treat Cerebrovascular Occlusive Disease, 191 Radiology 309 (1994)). The same concerns militate against other forms of therapy such as angioplasty for treatment of the carotid arteries. Various factors, including poor long-term patency, distal emboli causing a stroke, the potential for crushing from external pressure, and the need for long term anticoagulation, lead to the avoidance of certain stents in vessels smaller than the iliac arteries or in locations susceptible to external pressure. See, for example, Hull, The Wallstent in Peripheral Vascular Disease, For Iliac Use Only, 6 JVIR 884 (Nov.–Dec. 1995).

Stent-grafts have been proposed and used to treat aneurysms in the large blood vessels such as the aorta, and these typically include tube graft material supported by a metallic stent. These stent-grafts are designed for use in the large blood vessels, and the various layers of stents and grafts make them unsuitable for use in smaller blood vessels. Stent-grafts are not currently used in the coronary arteries which are typically 3 or 4 mm in internal diameter. Rolled stents have been proposed for use in aortic aneurysms. For example, Lane, Self Expanding Vascular Endoprosthesis for Aneurysms, U.S. Pat. No. 5,405,379 (Apr. 11, 1995) suggests the use of a polypropylene sheet placed in the abdominal or thoracic aorta to bridge aneurysms. Winston, Stent Construction of Rolled Configuration, U.S. Pat. No. 5,306,294 (Apr. 26, 1994) proposes a rolled sheet of stainless steel. Of similar construction are the single layer rolled stents such as Kreamer, Intraluminal Graft, U.S. Pat. No. 4,740,207 (Apr. 26, 1988) and its reissue Re 34,327 (Jul. 27, 1993), which are expanded by balloon and include a ratchet mechanism which projects into the lumen of the stent. Khosravi, Ratcheting Stent, U.S. Pat. No. 5,441,155 (Aug. 5, 1995) and Sigwart, Intravascular Stent, U.S. Pat. No. 5,443,500 (Aug. 22, 1995) are other examples of rolled stents with ratcheting locking mechanisms.

Stents have not previously been used for aneurysms of the blood vessels in the brain. The vessels in the brain likely to develop stenosis, aneurysms, AVM's and side branches requiring occlusion have diameters of about 1 mm to 5 mm, and can be accessed only via highly tortuous routes through the vascular system. The stents described below will be delivered percutaneously, introduced into the body through the femoral artery, steered upwardly through the aorta, vena cava, carotid or vertebral artery, and into the various blood vessels of the brain. Further insertion into the brain requires passage through the highly tortuous and small diameter intra-cranial blood vessels. The Circle of Willis, a network of blood vessels which is central to the intracranial vascular system, is characterized by numerous small arteries and bends. Passage of a stent from the internal carotid through the Circle of Willis and into the anterior cerebral artery (for example) requires a turn of about 60° through blood vessels of only 1–5 mm in diameter. Clinically, many significant aneurysms take place in the Circle of Willis and approaching blood vessels. The stent produced according to the methods described herein are intended for use in such highly tortuous vessels, particularly in the Circle of Willis, the vertebral and carotid siphons and other major blood vessels of the brain. At times, pathologically tortuous vessels may be encountered in the deeper vessels of the brain, and these vessels may be characterized by small diameter, by branching at angles in excess of 90° and by inaccessibility with guide wires larger than the standard 0.018 guide-wires. These pathologically tortuous vessels may also be subject to aneurysms and AVM's which can be treated with the stents produced according to the methods described below.

In order to fabricate sheet stents of extreme thinness, we have cold rolled metals such as Elgiloy, nitinol and stainless steel. Rolling appears to be effective to provide sheets of thickness down to 0.0011 inches. In order to fabricate thinner sheets, we have used chemical etching techniques to etch away even more of the sheet. This technique has enabled construction of sheets as thin as 0.0005" with somewhat uniform thickness. The method of constructing the stent described below, and the stent resulting from this method, will provide rolled sheet stents made according our prior disclosures in smaller and thinner dimensions than was previously possible. The fabrication method may be applied to all the stents previously used and proposed in the art, with the added advantage that stent is provided in a much thinner and/or stronger form, and may be constructed of nitinol or other metals and materials in a manner not previously used.

In the far-afield arts of micro-machines and microactuators, the fabrication of shape memory switches of microscopic proportions has been proposed. The fabrication technique is called sputter deposition. The resultant material is referred to as a thin film. The sputter-deposited films have been experimentally used in micro-valves and micro-grippers. Thin film sputtering processes are used in the manufacture of microchips to lay down very small and very thin circuit lines on circuit substrates such as silicon chips. Thin film processes are used to coat plastic articles with decorative chrome finishes. In general, thin film sputter techniques use high power electromagnetic fields to create energetic particles or photons (plasma ions, ion beams, electron beam, laser beam) directed toward a target plate of the coating material to dislodge single atoms or molecules of the coating material onto a substrate. The dislodged atoms or molecules condense on the substrate and adhere very strongly to the substrate. The sputter process is usually performed at very high temperature of one hundred to several hundred degrees centigrade, and performed within an atmosphere of very high vacuum and/or an atmosphere of an inert gas. Sputter techniques are part of a broader field of processes referred to as physical vapor deposition or PVD techniques. The PVD processes are part of the broader field of thin film deposition, which also includes chemical vapor deposition, and electroplating. The key to all these processes is the placement of the substrate (the article to be coated) in an atmosphere or cloud of film molecules.

SUMMARY

The rolled sheet stents which we have proposed for use in very small blood vessels of the brain may be constructed according to thin film sputtering techniques. Rather than roll metals to the desired thickness, which may be on the order of several thousands of an inch and thinner, the stent is created by sputtering hot molten metal onto a mold substrate. This results in a stronger sheet of metal vis-à-vis the rolling process. Rather than mechanically or photochemically cut the desired perforations into the sheet, the perforations are formed during the sputtering process as areas which are not sputtered. When the stent is made of nitinol by thin film sputtering techniques, the resultant sheet may be cured at high temperature to provide a stent with the same pseudoelastic or shape memory properties as found in bulk prepared rolled sheets of nitinol. Thin sheets of nitinol, with a uniform thickness of 0.0002 inches and less, can be made with this technique. The specific embodiment of thin film deposition used to exemplify the invention is RF powered physical vapor deposition. However, the various techniques of thin film deposition may be used.

Rolled sheet stents are preferably provided with dense perforation patterns, as illustrated in Wallace, et al, Intracranial Stent and Method of Use, PCT App. PCT/US97/16534. These perforation patterns have been made using a photochemical machining process which includes coating the sheet with a photoresist coating, processing the photoresist coating to remove the coating in areas corresponding to the desired perforations, thereby creating a partial coating which is a reverse image of the desired perforation pattern on the sheet, etching the metal in the uncoated areas with a chemical etchant to remove the metal in the areas corresponding to the desired perforation pattern, and then stripping the photoresist coating. This allows the creation of such thin sheets of metal without resort to mechanical cutting. By manufacturing the stent with a sputtering technique, the perforation patterns can be created by control of the deposition of the sputtered metal, thus eliminating the need for that the stent be subjected to photochemical machining process after its formation.

DETAILED DESCRIPTION OF THE INVENTION

Figure 1:
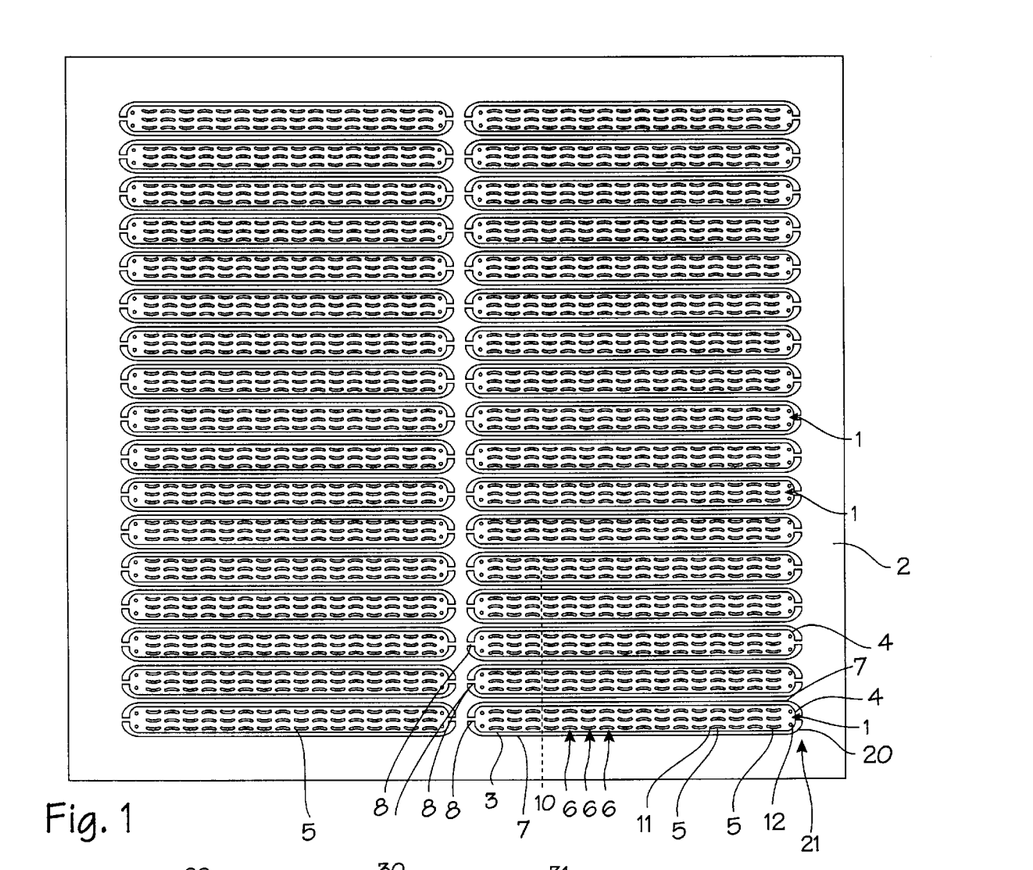
FIG. 1 is example of a stent to be formed with the sputtering technique
Figure 2:
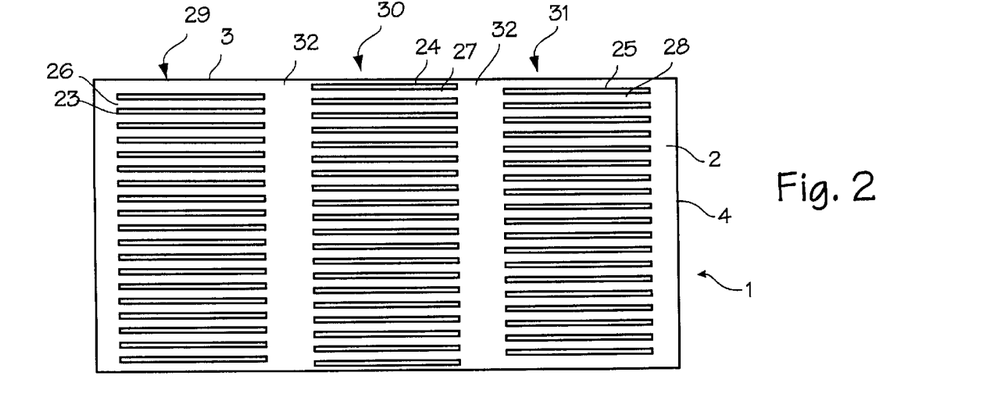
FIG. 2 is example of a stent to be formed with the sputtering technique

The thin film deposition processes may be used to fabricate a number of medical devices. FIGS. 1 and 2 illustrate a stent which may be formed by the process detailed below. Although the stent may be made in many forms, these two stents illustrate the structural elements to be formed by the sputtering process.

FIG. 1 shows a basic form of the stent 1 as formed on a sheet of stents. (The various item mentioned below are so numerous in the stent sheet that they are called out on the drawing only in exemplary parts.) The stents are formed in a sheet 2 of nitinol, Elgiloy™, stainless steel, plastic or other suitable material. For stents fabricated for use in small blood vessels, the wrap length represented by transverse edge 3 will be about 6–75 mm, allowing the stent to expand to diameters from about 1 mm to about 6 mm with approximately two to three layers of overlap after expansion. The bridge length represented by axial edge or axial width 4 (or the longitudinal edge) will vary according to the width of the aneurysm, occlusion or other defect which must be bridged by the stent, and may vary from 2 to 20 mm, for example. The stent is formed as a flat sheet. The stent is tempered or formed so that, when rolled and released, it resiliently unrolls and expands to a diameter of approximately 1 mm to 6 mm, and provides a slight compliance mismatch with the intra-cranial arteries which have internal diameters of about 1 mm to 6 mm. Where the stent is made of nitinol, the nitinol may have an austenitic transition temperature $T_{af}$ of about 30° C. (slightly below body temperature of 37° C.), so that expansion is entirely due to the resilience of the austenite phase, or it may have a transition temperature slightly above body temperature so that expansion may be cause by application of heat, or it may be provided in a superelastic form so that expansion is due to superelastic or pseudoelastic behavior of the film.

The stent 1 is provided with a number of perforations 5. They may be formed more specifically as a series of partial sinusoidal curves. The multitude of perforations 5 are provided in sets 6 disposed between straight radial slits 7 in the sheet. The radial slits 7 in the sheet 2 leave trim tabs 8, which keep the stents attached to the sheets during the etching process and during other preparation processes, after which they are cut through to remove the finished stents from the sheet. The perforations are crescent shaped, arcuate, but may be wave-shaped or "s" shaped in general appearance. The perforations are about 0.03–0.07 inches apart radially, and 0.02634 inches apart longitudinally, and they are about 0.00625 inches wide and 0.06102 inches long. The perforations extend circumferentially, aligned generally with the wrap length, while the groups of sets 6 extend along the bridge length 4 of each stent. The groups of curves creates longitudinal staves of unperforated sheet material along longitudinal line such as line 10. These staves are relatively stiff compared to the perforated area. The curves are not significantly inclined away from or toward the wrap length or transverse edge 3, so that a multiple number of circumferentially extending and sinusoidally winding strips of sheet material are formed within the stent. The strips are not perfectly sinusoidal, but may generally be described as sinusoidal, wavy, sinuous or wiggled in a manner where the long path of the strip is generally straight, but regularly deviates away from the long path. In FIG. 1, end endpoints 11 of the perforations in respective sets are longitudinally aligned, meaning that they appear at the same point along the length 4 of the stent. The retaining perforations 12 are used to retain the stent on an insertion catheter.

The long radial or circumferential slits 7 are generally straight in the circumferential direction, except for the curve 20 toward the longitudinal dimension of the stent which is incorporated at the terminus 21 of each radial slit. The rounded edges thereby created in the radial end of the stents help distribute the point force imparted on the vessel wall and reduces the risk of vascular injury that arises with the use of square edges. The pair of circular perforations 22 is provided for threading a retention/release wire through the stent sheet while rolled upon an insertion catheter.

FIG. 2 shows the stent 1 with a different perforation scheme, with cutaways 23, 24 and 25 leaving slats or ribs 26, 27, and 28 in eventual outer layer 29, middle layer 30 and inner layer 31. The segments of slats are separated by spines or backbones 32. The slats of each segment are offset so that, when expanded to a roll of approximately three layers, the three layers will overlap to form a barrier between the blood vessel wall and the inner lumen of the expanded stent.

Figure 3:
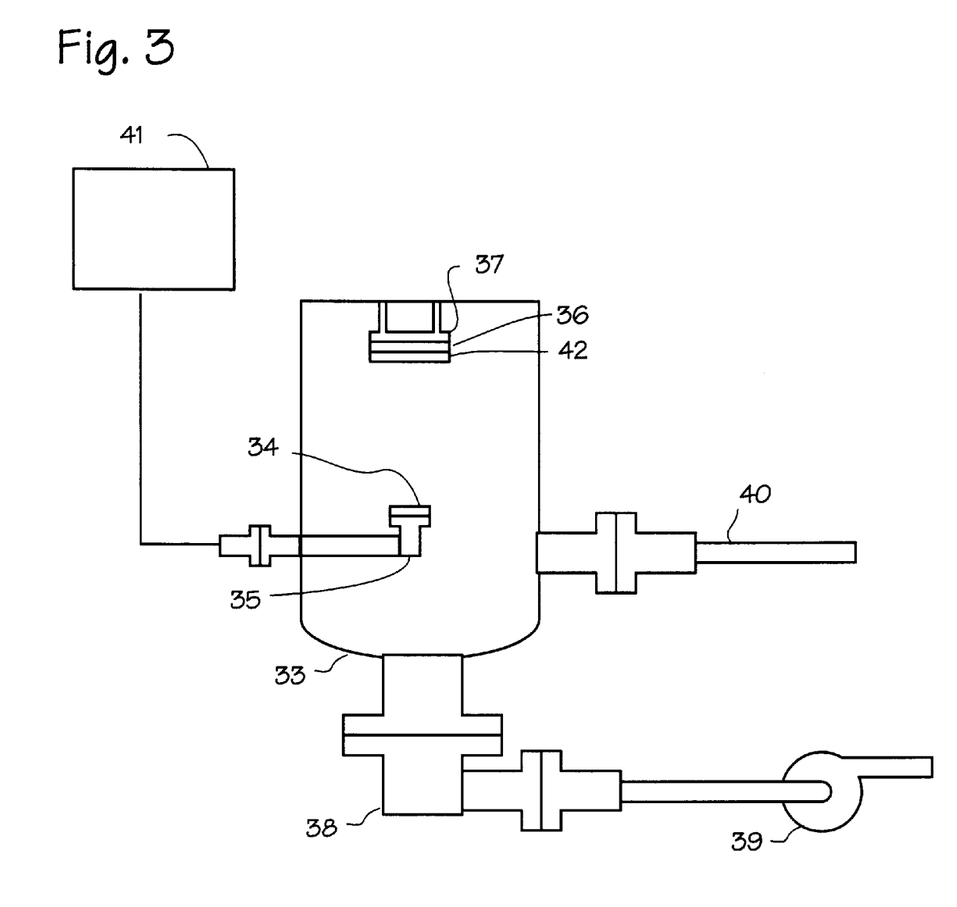
FIG. 3 is schematic of the process of sputtering a thin sheet of nitinol.

With these structural parts of the stent in mind, the process of fabricating the stent through the physical vapor deposition technique of sputtering may be described. FIG. 3 illustrates the basic process of forming the stent with sputtering techniques. (The process is sometimes referred to as glow discharge sputtering.) The sputter deposition may be accomplished with several methods, all of which have the same basic method steps and use analogous equipment. The device for accomplishing the sputtering includes a reaction chamber 33 which houses the target 34, mounted on the target mount 35 and the substrate 36 mounted on the substrate holder 37. The reaction chamber is capable of holding a strong vacuum, created by operation of vacuum pumps 38 and 39. A very low pressure Argon atmosphere is created with the injection of Argon gas through the argon supply line 40 (other inert gases can be used). The power source 41 is capable of applying high negative voltage RF or DC power to the target 34. The intense electric field ionizes the Argon, separating the gas atoms into positively charged argon atoms and negatively charged electrons. The positively charged Argon atoms are attracted to the negatively charged target, and accelerate toward the target at high energy. In this system, the target acts as the cathode, and the chamber acts as the anode, attracting the free electrons of the plasma. The substrate may be placed anywhere in the system. (The substrate may be connected as the ground of the power system and act as the anode so that is intercepts a larger portion of the sputtered material.) When the argon ions hit the target 34 at high energy, they dislodge an atom or molecule of the target material from the target. This atom or molecule of the target material is propelled from the target material into the chamber, and some of the dislodged atoms settle onto substrate 36, where they condense on the surface. In this fashion, a film 42 of the target material is build up on the substrate, one atom at a time. Perkin Elmer sputtering systems used by various sputtering shops are typical of the systems available for accomplishing the sputtering process.

In the sputtering art, the substrate may be a silicon wafer, a microchip, or other partially complete product. In our case, the substrate will be discarded at the end of the fabrication process. The substrate used for stent fabrication may be made of silicon or glass, highly polished metals such as aluminum, salts such as sodium chloride or potassium bromide, or plastic (and many other materials). The substrate may be made of fluorite ($CaF_2$), which does not bond well to titanium, and therefore eases eventual removal of the stent from the substrate. The substrate may include an oxide layer and a layer of waste material upon which the sputtered material is deposited. The target material is generally the same as the stent (its atoms and molecules are transferred from the target onto the substrate to form the stent). Thus a target comprising nitinol will produce a thin film of nitinol on the substrate upon bombardment. Where the stent is an alloy such as nitinol, the target may be pre-alloyed NiTi having the desired transition temperatures. The target may be comprised of two distinct targets, one titanium and one nickel, where the alloying is accomplished by sputtering both metals in successive sputters over the substrate (the metal will alloy together upon deposition and annealing, which is a desired process in any case). Other common stent materials including stainless steel, tantalum, Elgiloy and even polymers may be used.

Other sputtering techniques are variations on this basic technique. In ion beam sputtering, the ion beam is created using a ion beam gun. The ion beam gun directs a stream of ions at the target material to dislodge target atoms. The substrate is place in the chamber near the target to collect the dislodged atoms. In this system, the target is not electrified. The process of vacuum evaporation uses the combination of heat and very low pressure to evaporate or sublime the target in the vicinity of the substrate, so that the evaporated target molecules condense on the substrate. The heat may be provided thermally, through resistive heating of the target, or by irradiating the target with laser energy from a laser, an electron beam emitted from an electron beam emitter. Vacuum evaporation deposition is a line of sight deposition technique. For some stent compositions, chemical vapor deposition may be used. Chemical vapor deposition permits reaction of chamber atmosphere components with each other or with ejected target material to form the deposited compound.

The process of cold sputtering can be used with a plastic substrate, in order to form a stent on a rather inexpensive substrate made of plastic. Plastic substrates may be made of ABS plastic (acrylonitrile-butadiene-styrene copolymer), polyimide resins, polyethylene terephthalate resins and other plastics. Sputtering may be accomplished in typical cold sputter ranges (extremely low pressure argon atmosphere, 200–600 volt applied to the cathode), with current density limited to the range of about 0.2 to 5 $A/dm^2$. After the thin film is sputter deposited on the plastic substrate, the stent may be removed for the plastic substrate by dissolving the plastic in a solvent.

Figure 4:
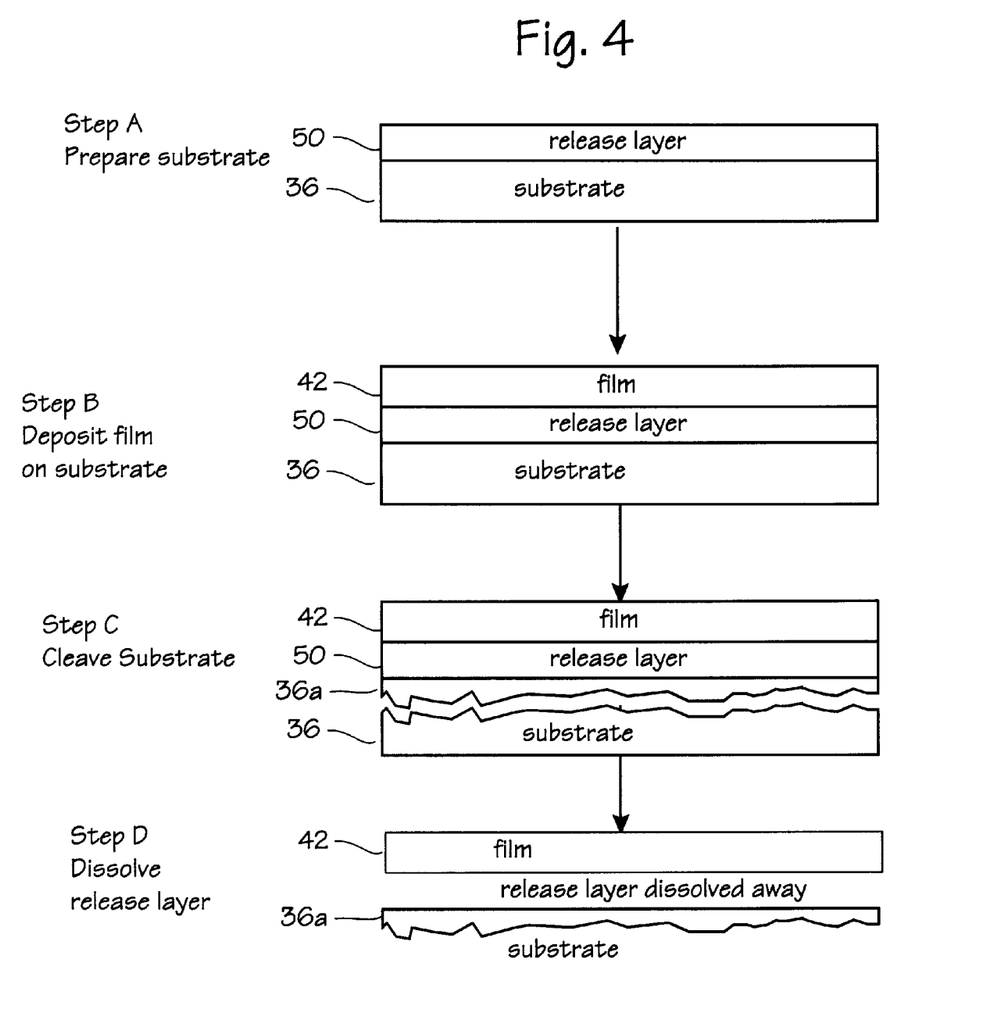
FIG. 4 illustrates the processing necessary to create a thin film of nitinol which can be released from the substrate.

FIG. 4 illustrates the process of forming and removing the stent from the substrate. In step A, the substrate 36 with a release layer 50 (an oxide layer on a silicon substrate, for example) is provided within the reaction chamber. In step B, the substrate is exposed to the sputter in the reaction chamber and a thin film of nitinol is gradually built up on the substrate. This film corresponds to the sheet 2, and may be about 1 to 30 microns thick for use in intracranial blood vessels (and thicker for larger vessels). The substrate 36 is typically unchanged in size after deposition. The substrate, when made of silicon or metal, can include the thin layer of oxide on the substrate material (but some useful substrates do not oxidize). This oxide layer may be formed intentionally on the substrate prior to sputtering, or it may merely be the result of oxidation during normal handling of the substrate.

Referring again to FIG. 4, after the stent sheet is formed on the substrate, it must be removed in one piece in order to be used in the body. Several methods may be used to remove the stent, some of which depend on the choice of substrate material. Where the thin film is highly adherent, such as when sputtered on a silicon or aluminum substrate, a release layer of non-adherent or readily dissolvable material such as oxides or nitrides are placed on the substrate before sputtering acts as a release layer. This will facilitate removal of the film for use as the stent sheet. The oxide layer can be formed on silicon, for example, by exposing the silicon to water vapor at high temperature for several hours.

To remove the thin film stent in this example, in Step C the nitinol thin film can be separated from the substrate by shearing the silicon oxide/silicon substrate boundary (rapid cooling or heating will initiate a thermal shock that will crack or shear the composite at the boundary). This will result in a composite of the nitinol thin film 42, the silicon oxide 50, and a very thin layer of silicon substrate 36. In Step D, the thin film is converted into the free standing stent by removing the silicon oxide layer by etching the intermediate composite in a solution of hydroflouric acid until the silicon oxide is dissolved and the silicon has fallen away. The nitinol thin film remains as a free standing thin film after the silicon oxide has been etched away. The hydroflouric acid used in this process will also serve to etch or pickle away any nitinol oxides from the nitinol. (Alternative release layers can be used. The release layer may be comprised of silicon nitrides, which can be etched away with a CF4/O2 plasma etch without damaging the nitinol thin film. (Where aluminum is used as the substrate, aluminum oxide may be permitted or encouraged to form on the substrate, and the substrate may be dissolved away with a solution of sodium hypochloride and sodium hydroxide. Aluminum without an oxide layer may be used, and dissolved away with a variety of acids and bases (hydrochloric acid, phosphoric acid, acetic acid, nitric acid). Where salts are used as the substrate, they may be dissolved in water.

Another method for creating a releasable thin film is to use the following method for sputtering: A nitinol target of approximately 50 atomic percent titanium (depending on the desired transition temperature in the finished stent) is used. A substrate of silicon, glass copper, aluminum, kapton film or other material is located anywhere from 2 to 8 inches from the target. The substrate is preferably oxidized, through an oxidation step designed to enhance the oxide layer (this step may comprise merely exposing the substrate to air). The chamber atmosphere is set at about 1 millitor and cathode power is set from about 250 to 400 watts. The substrate is maintained or permitted to remain at chamber temperature, which should be slightly elevated over ambient air temperature (normal room temperature of about 22°). The film may then be lifted from the substrate merely by laying an adhesive strip over the film and pulling the film off the substrate. (Those in the sputter deposition art will appreciate that the typical step of chemically etching the substrate to remove the oxide layer need not be performed.)

The stent film may be annealed to obtain the desired material characteristics of the nitinol alloy, namely the shape memory, superelastic and pseudoelastic behaviors. The annealing may be accomplished before or after removal of the stent film from the substrate. Annealing the stent sheet can be accomplished according to standard annealing methods, which typically required a period of several minutes at temperatures around 500° centigrade. Where the substrate melts at the annealing temperature (as it the case with plastics), it may be removed either before the annealing process, or it may be melted away during the annealing process. The annealing process may help separate the thin film from the substrate where it is undertaken prior to release of the thin film from the substrate.

The perforation pattern on the stent sheet may be created with several methods. The perforations may be photochemically etched into the nitinol film after formation of the film into stent sheet, or the release layer may be etched and undercut with subsequent sputter deposition onto the remaining top surface of the release layer.

Figure 5:
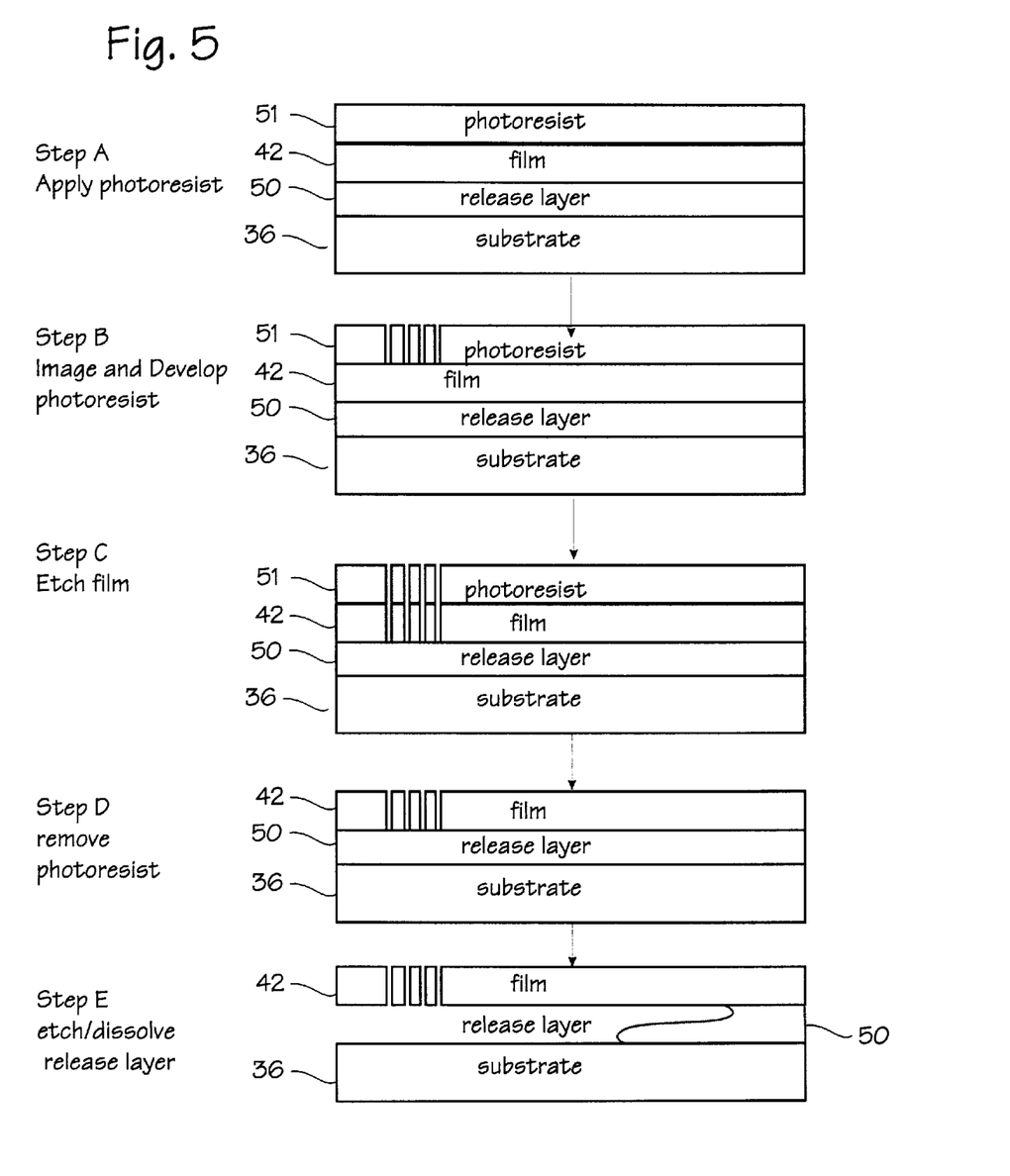
FIG. 5 illustrates the processing necessary to perforate the thin film for use as a microporous stent.

The process of photochemical machining may be used to cut the perforations in a solid sheet of nitinol thin film. Photochemical etching may be accomplished either before or after the nitinol thin film is lifted from the substrate. As shown in FIG. 5, in step A the thin film stent sheet 2 is still mounted on the substrate 36, and the sheet is coated with a layer of photoresist 51. In step B, the photoresist is processed (imaged and developed) to remove the coating in areas corresponding to the desired perforations, thereby creating a partial coating which is a reverse image of the desired perforation pattern on the sheet, and essentially a copy of the desired final perforated stent sheet. In step C, this intermediate composite is then soaked with an etchant for the nitinol which preferably does not react with the underlying substrate or oxide layer. Suitable etchants include hydrofluoric acid, and BOE, $HNO_3$, $H_2O$ solution. In step D, after the etchant has removed the stent sheet material in the perforation areas, the photoresist is removed with a wash of a suitable etchant which dissolves the photoresist (there are numerous photoresists and corresponding etchants. The remaining composite is the same as the initial composite, except that the nitinol thin film is now perforated. In Step E, the release layer 50 is removed and the nitinol film is now a free standing stent perforated as desired.

The process of forming the thin film stent with perforations may be modified so that the perforations are created during the deposition process. Rather than etch the finished thin film to create the perforations, the substrate may be coated with a waste layer (using a photoresist compound or other etchable compound) which is etched with a reverse image of the stent, and the stent film may be deposited over the reverse image waste layer. The process is a lift off technique similar to techniques used in microprocessor fabrication.

Figure 6:
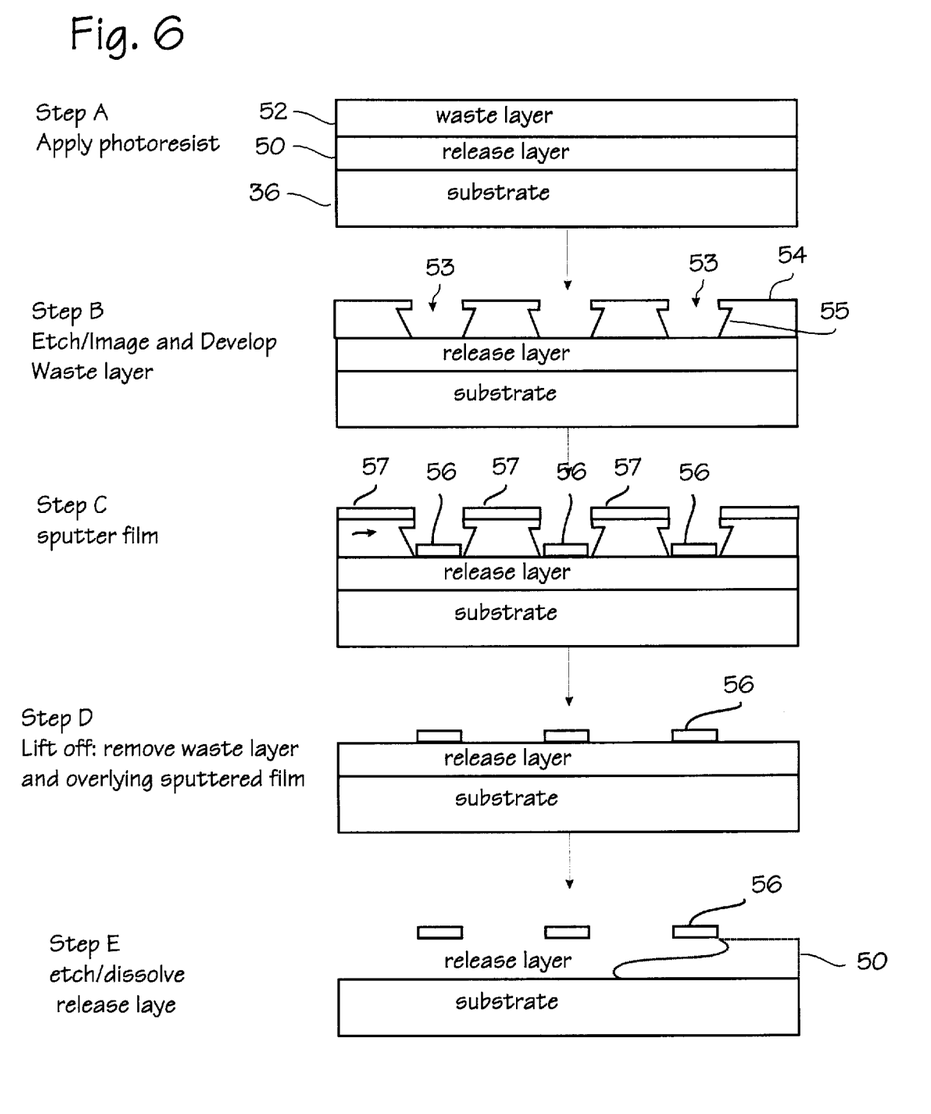
FIG. 6 illustrates the processing depositing a perforated thin film for use as a microporous stent.

The process is illustrated in FIG. 6. At step A, the substrate 36, removable oxide layer 50 are coated with a waste layer 52. The waste layer may be comprised of a photoresist compound or other readily removable material. If made of a photoresist, the waste layer is imaged (exposed and developed) with a reverse image of the desired stent. At step B, the waste layer has numerous perforations 53 which correspond to the actual structure of the stent, and numerous strips and coated areas 54 which correspond to the perforations of the stent. The side walls 55 of the coated areas are undercut (to this end, the waste layer may be comprised of two layers, a top layer which is imaged and developed, followed by non-directional etching or wet etching of the underlying layer). The process creates a reverse slope photoresist side-wall profile. In step C, the stent material is sputtered with a line of sight deposition technique which avoids coating the side walls 55 (in contrast to step coverage or conformal coverage). The result is a layer of thin film of nitinol 56 on the substrate and a thin film of nitinol 57 on the waste layer. The film 56 on the substrate is the stent, formed as desired with perforations, struts, staves, and border areas as dictated by the reverse image in the photoresist applied in step B. In step D, the waste material is dissolved and removed, along with waste film 57 sputter on top of the waste material. In step E, the silicon oxide layer 50 is dissolved away to remove the fully formed stent from the substrate.

Various photoresists may be used as the waste material, and numerous other compounds may be suitable. Where the photoresist is AZ-5214-E or equivalent, it may be removed in the final step with an ultrasonic cleaning in a bath of acetone. The waste layer may also be made of silicon nitride, removed with a phosphoric acid etch. The material "lifted off" is the waste nitinol deposited on the areas corresponding to the perforations in step D. The portion of the film left on the substrate is also lifted off, but preserved as the desired end produce.

Figure 7:
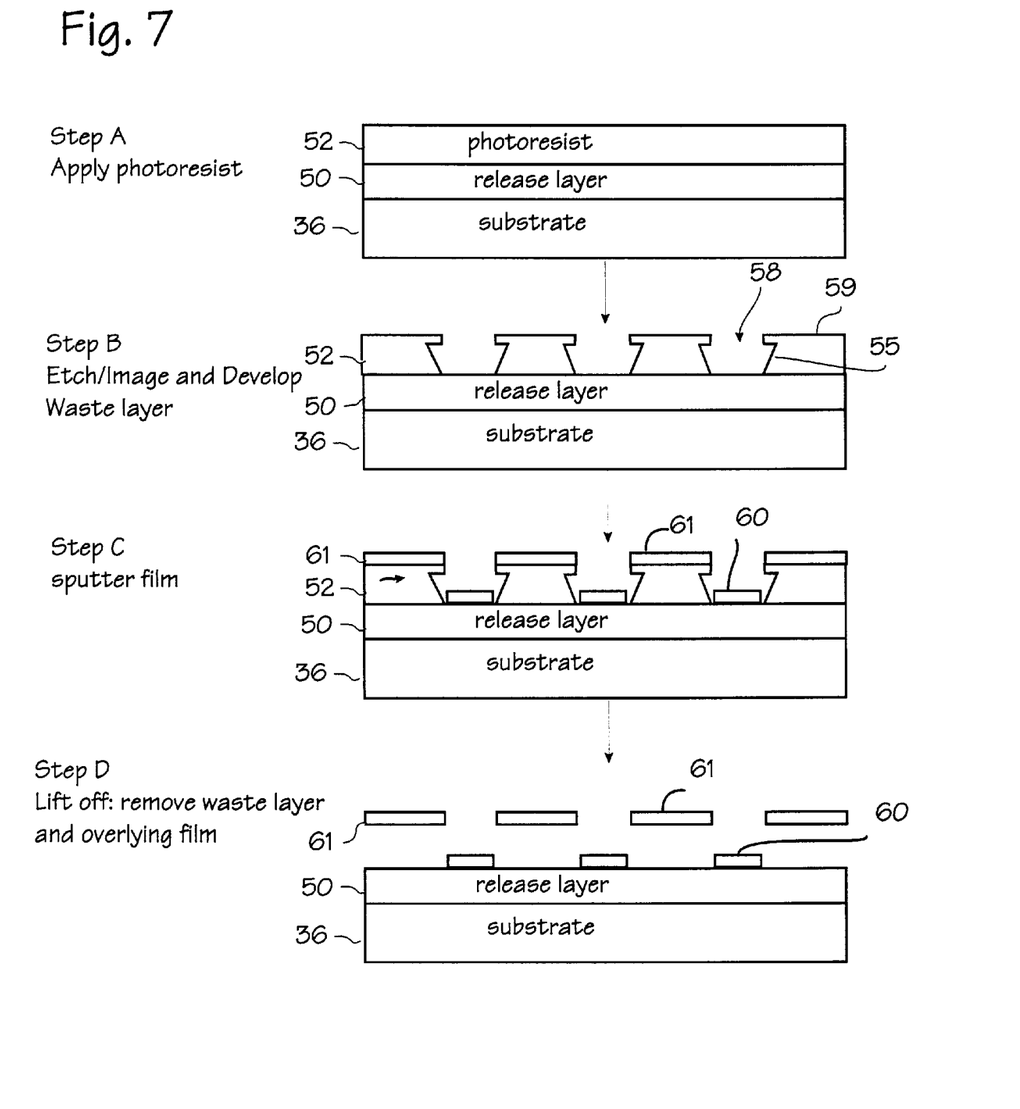
FIG. 7 illustrates the processing depositing a perforated thin film for use as a microporous stent.

The lift off process places the waste nitinol material over the waste layer 52, and sputters the desired film onto the substrate. The process may be reversed as illustrated in FIG. 7 as follows: At step A, the substrate 36 and removable oxide layer 50 are coated with a waste layer 52. The waste layer may be comprised of a photoresist compound or other readily removable material. If made of a photoresist, the waste layer is imaged (exposed and developed) with positive (rather that a reverse) image of the desired stent. At step B, the waste layer has numerous perforations 58 which correspond to the actual perforations of the stent, and numerous strips and coated areas 59 which correspond to the actual structural elements of the stent. In step C, the stent material is sputtered with a line of sight deposition technique which avoids coating the side walls 55. The result is a layer of thin film of nitinol 60 on the substrate and a thin film of nitinol 61 on the waste layer. The film 60 on the substrate is the wasted thin film stent, while the film 61 on the waste layer is the stent, formed as desired with perforations, struts, staves, and border areas as dictated by the positive image in the photoresist applied in step B. In step D, the photoresist is dissolved away in a bath of acetone or other solvent. In this process, the material "lifted off" is the desired stent. In either process of lift off or reverse lift off, the photoresist may be a positive (exposed areas become soluble) or negative photoresist (exposed areas become insoluble) which may be exposed with a positive or reverse image of the desired stent. Thus, where the waste perforations are lifted off (leaving a positive on the substrate), and the waste material is a positive photoresist, the photoresist is exposed in areas corresponding to the stent structure (rather than the perforations) and the photoresist is developed to remove the exposed areas. Where the wasted stent material is lifted off and the waste material is a negative photoresist, the photoresist is exposed in areas corresponding to the stent perforations (rather than the structure) and the photoresist is developed to remove the unexposed areas. Where the waste perforations are deposited on the substrate and the actual stent is deposited on the waste material, and the waste material is a positive photoresist, the photoresist is exposed in areas of perforation and the photoresist is developed to removed exposed areas. Where the waste perforations are deposited on the substrate and the actual stent is deposited on the waste material, and the waste material is a negative photoresist, then the photoresist is exposed in areas of stent structure and the photoresist is developed to remove unexposed areas.

The strength and resilience of the stent may be improved with hot isostatic processing (HIP or hipping) of the stent to remove voids in the sputtered stent and increase the density of the stent. In this process, after the sputtered stent has been released from the substrate and etched to form the perforation patterns, it is placed in a HIP chamber for exposure to a high pressure, high temperature atmosphere of inert gas (argon) to eliminate any voids in the thin film. Temperatures up to 2000° C. and pressures up to 650 MPa (94,000 psi) may be applied in the process, and the pressure and temperature may be applied for variable time periods of minutes to hours, depending on how long it takes for the voids in the stent to fill. After hipping, the thin film can be additionally strengthened by cold working, for example by pack rolling the thin film in one or more passes through a thin film roller. (Since hipping generally increases fatigue life of the hipped article, is may beneficially be used with all stents, implanted prostheses and other medical devices subject to repetitive stress. It may also be beneficially applied to sputtered nitinol actuators generally, such as the micro-valves and micro-grippers mentioned in the background.)

The process of forming a rolled sheet stent according to the description may be varied in many particulars. While we have illustrated the process with the example of a nitinol stent, any metal and many polymers can be sputtered into the thin film. While we have illustrated the broader invention of creation of a free standing thin film medical device with the example of a stent, various other devices may be created with the process. While we have used the specific example of physical vapor deposition through sputtering, the many forms of thin film deposition may be used. We expect that more desirable substrates, release layers, waste layers and target compositions may be discovered and applied in the making stents and medical devices according to the inventive methods presented above. Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

I claim:

1. A method for manufacturing a body implantable stent, said method comprising:

providing a substrate susceptible to degradation upon application of a substrate etchant;

sputter depositing a thin film of material onto the substrate;

applying a substrate etchant to the substrate to degrade the substrate, thereby releasing the thin film of material from the substrate; forming the thin film of material into a stent.

2. The method of claim 1 further comprising:

photochemically machining a pattern of perforations into the thin film before releasing the thin film of material from the substrate.

3. The method of claim 1 wherein:

the substrate used is comprised of silicon;

the material which is sputter deposited is nitinol;

the silicon substrate is provided with a layer of silicon oxide, and the thin film is deposited over the layer of silicon oxide;

the substrate etchant is applied to dissolve the layer of silicon oxide, thereby releasing the thin film from the substrate.

4. The method of claim 3 further comprising:

photochemically machining a pattern of perforations into the thin film.

5. The method of claim 3 further comprising:

photochemically machining a pattern of perforations into the thin film, performing said photochemical machining before releasing the thin film from the substrate.

6. The method of claim 3 further comprising:

photochemically machining a pattern of perforations into the thin film, wherein said step of photochemically machining a perforation pattern comprises the steps of (1) applying a photoresist coating on the surface of the thin film, (2) removing the photoresist in the areas of desired perforations (3) chemically etching the thin film in film etchant to remove the thin film material under the areas of desired perforations and (4) removing the photoresist from the surface of the thin film.

7. The method of claim 3 further comprising:

photochemically machining a pattern of perforations into the thin film before removing the thin film from the substrate, wherein said step of photochemically machining a perforation pattern comprises the steps of (1) applying a photoresist coating on the surface of the thin film, (2) removing the photoresist in the areas of desired perforations (3) chemically etching the thin film in film etchant to remove the thin film material under the areas of desired perforations and (4) removing the photoresist from the surface of the thin film.

8. A method of forming a stent comprising:

providing a target comprising a material;

providing a thin film deposition chamber capable of removing molecules from the target;

providing a substrate and placing the substrate within the thin film deposition chamber;

operating the thin film deposition chamber to remove molecules from the target and cause said removed molecules to condense on the substrate and form a deposited film on the substrate;

releasing a deposited film from the substrate; forming the deposited film into a stent.

9. The method of claim 8 further comprising:

perforating the stent through a photochemical etching process.

10. The method of claim 8, further comprising the steps of:

prior to forming the deposited film on the substrate, coating the substrate with a layer of waste material;

photochemically etching the layer of waste material to impart a pattern of perforations in the waste material;

thereafter forming the deposited film on the substrate coated with the etched layer of waste material; and removing the waste material.

11. The method of claim 8, further comprising the steps of:

after forming the deposited film on the substrate, coating the deposited film with a layer of photoresist;

imaging and developing the layer of photoresist to impart a pattern of perforations in the photoresist, leaving areas of the deposited film exposed;

etching the deposited film with an etchant to remove exposed portions of the deposited film.

12. The method of claim 10, wherein the etching of the deposited film is done prior to removal of the medical device from the substrate.

13. The method of claim 8, where the target is comprised of nitinol.

14. A method of forming a stent comprising: providing a target comprising a material; providing a sputter deposition chamber capable of removing molecules from the target; providing a substrate and placing the substrate within the sputter deposition chamber; operating the sputter deposition chamber to remove molecules from the target and cause said removed molecules to condense on the substrate and form a deposited film on the substrate; releasing the deposited film from the substrate; forming the deposited film into a stent; hipping stent.

* * * * *